US00PP17927P2

(12) United States Plant Patent

Bergman

(10) Patent No.: US PP17,927 P2

(45) Date of Patent: Aug. 14, 2007

(54) *CHRYSANTHEMUM* PLANT NAMED 'YOCHATHAM'

(50) Latin Name: *Chrysanthemum×morifolium*
Varietal Denomination: Yochatham

(75) Inventor: Wendy R. Bergman, Lehigh Acres, FL (US)

(73) Assignee: Yoder Brothers Inc., Barberton, OH (US)

( * ) Notice: Subject to any disclaimer, the term of this patent is extended or adjusted under 35 U.S.C. 154(b) by 71 days.

(21) Appl. No.: 11/269,173

(22) Filed: Nov. 8, 2005

(51) Int. Cl.
*A01H 5/00* (2006.01)

(52) U.S. Cl. ..... Plt./287

(58) Field of Classification Search ..... Plt./287
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Chrysanthemum* plant named 'Yochatham', characterized by its compact, upright, outwardly spreading and mounded plant habit; strong and freely branching growth habit; dark green-colored foliage; uniform flowering response and habit; early and freely flowering habit; decorative-type inflorescences with elongated oblong-shaped and light purple-colored ray florets; and good post-production longevity with plants maintaining good substance and color for about there weeks in an interior environment.

2 Drawing Sheets

Botanical designation: *Chrysanthemum×morifolium.*
Cultivar denomination: 'Yochatham'.

BACKGROUND OF THE INVENTION

The present Invention relates to a new and distinct cultivar of *Chrysanthemum* plant, botanically known as *Chrysanthemum×morifolium* and hereinafter referred to by the name 'Yochatham'.

The new *Chrysanthemum* is a product of a planned breeding program conducted by the Inventor in Salinas, Calif. and Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response and good post-production longevity.

The new *Chrysanthemum* originated from a cross-pollination made in February, 2000 in Salinas, Calif., of a proprietary selection of *Chrysanthemum×morifolium* identified as code number YB-A0517, not patented, as the female, or seed, parent with a proprietary selection of *Chrysanthemum×morifolium* identified as code number YB-6474, not patented, as the male, or pollen, parent. The new *Chrysanthemum* was discovered and selected by the Inventor as a single flowering plant within the progeny of the stated cross-pollination grown in a controlled environment in Alva, Fla. in December, 2001. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Alva, Fla. in March, 2002. Asexual reproduction by cuttings has shown that the unique features of this new *Chrysanthemum* are stable and reproduced true to type in successive generations.

SUMMARY OF THE INVENTION

The cultivar Yochatham has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yochatham'. These characteristics in combination distinguish 'Yochatham' as a new and distinct *Chrysanthemum:*

1. Compact, upright, outwardly spreading and mounded plant habit.
2. Strong and freely branching growth habit.
3. Dark green-colored foliage.
4. Uniform flowering response and habit.
5. Can be grown as a spray-type or without bud removal.
6. Early and freely flowering habit.
7. Decorative-type inflorescences with elongated oblong-shaped ray florets.
8. Light purple-colored ray florets.
9. Good postproduction longevity with plants maintaining good substance and color for about three weeks in an interior environment.

Plants of the new *Chrysanthemum* can be compared to plants of the female parent selection. Plants of the new *Chrysanthemum* differ from plants of the female parent selection in the following characteristics:

1. Plants of the new *Chrysanthemum* are more compact than plants of the female parent selection.
2. Plants of the new *Chrysanthemum* have smaller inflorescences than plants of the female parent selection.

Plants of the new *Chrysanthemum* can be compared to plants of the male parent selection. Plants of the new *Chrysanthemum* differ from plants of the male parent selection in the following characteristics:

1. Plants of the new *Chrysanthemum* and the male parent selection differ in ray floret coloration as plants of the male parent selection have red-colored ray florets.
2. Inflorescences of plants of the new *Chrysanthemum* produce few disc florets whereas inflorescences of plants of the male parent selection produce many disc florets.

Plants of the new *Chrysanthemum* can be compared to plants of the cultivar Yopresidio, disclosed in U.S. Plant Pat. No. 13,896. In side-by-side comparisons conducted in Alva, Fla., plants of the new *Chrysanthemum* differed from plants of the cultivar Yopresidio in the following characteristics:

1. Plants of the new *Chrysanthemum* were more compact than plants of the cultivar Yopresidio.
2. Plants of the new *Chrysanthemum* were more outwardly spreading than plants of the cultivar Yopresidio.
3. Plants of the new *Chrysanthemum* and the cultivar Yopresidio differed in ray floret color as plants of the cultivar Yopresidio had pink-colored ray florets.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yochatham' grown as spray-types.

The photograph on the second sheet comprises a close-up view of typical inflorescences of 'Yochatham' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the summer in Salinas, Calif., in a fiberglass-covered greenhouse and under conditions which approximate those generally used in commercial potted *Chrysanthemum* production. During the production of these plants, the following conditions were measured: day temperatures, 21° C. to 27° C.; night temperatures, 17° C. to 19° C.; and light levels, 5,000 to 6,000 foot-candles. Four unrooted cuttings were directly stuck in 15-cm containers, exposed to long day/short night conditions, and pinched once about two weeks later. About one week after the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yochatham.

Commercial classification: Decorative-type potted *Chrysanthemum.*

Parentage:

*Female, or seed, parent.*—Proprietary selection of *Chrysanthemum×morifolium* identified as code number YB-A0517, not patented.

*Male, or pollen, parent.*—Proprietary selection of *Chrysanthemum×morifolium* identified as code number YB-6474, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Compact herbaceous decorative-type potted *Chrysanthemum* that can be grown as a spray-type or without bud removal. Upright with lateral branches outwardly spreading; uniformly mounded crown. Strong and freely branching growth habit; about five lateral branches develop after removal of terminal apex (pinching); dense and full plants.

*Plant height.*—About 23 cm.

*Plant width.*—About 37 cm.

*Lateral branches.*—Length: About 19 cm. Diameter: About 4.5 mm. Internode length: About 1.3 cm. Strength: Strong. Texture: Pubescent. Color: 146A.

*Foliage description.*—Arrangement: Alternate; simple. Length: About 5.3 cm. Width: About 4 cm. Apex: Cuspidate. Base: Truncate with attenuate tendencies. Margin: Palmately lobed, sinuses between lateral lobes parallel to convergent. Texture, upper and lower surfaces: Pubescent. Color: Developing and fully expanded foliage, upper surface: Close to 147A. Developing and fully expanded foliage, lower surface: Close to 147B. Venation, upper and lower surfaces: Close to 147B. Petiole length: About 1.6 cm. Petiole diameter: About 2.5 mm. Petiole texture, upper and lower surfaces: Pubescent. Petiole color, upper surface: Close to 146B. Petiole color, lower surface: Close to 146B to 146C.

Inflorescence description:

*Appearance.*—Decorative-type inflorescence form with elongated oblong-shaped ray florets. Inflorescences borne on terminals above foliage. Disk and ray florets develop acropetally on a capitulum. Inflorescences faintly fragrant.

*Flowering response.*—Upper natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to three weeks of long day/short night conditions followed by photoinductive short day/long night conditions flower about eight weeks later.

*Postproduction longevity.*—Inflorescences maintain good color and substance for about three weeks in an interior environment.

*Quantity of inflorescences.*—About eight inflorescences per lateral branch.

*Inflorescence bud.*—Height: About 5 mm. Diameter: About 4 mm. Shape: Oblate. Color: Close to 146A to more green than 147A.

*Inflorescence diameter.*—About 4.75 cm.

*Inflorescence height.*—About 1.5 cm.

*Diameter of disc.*—About 2.5 mm; inconspicuous.

*Receptacle diameter.*—About 5 mm.

*Receptacle height.*—About 4 mm.

*Ray florets.*—Length: About 2.3 cm. Width: About 5 mm. Corolla tube length: About 3 mm. Corolla tube diameter: About 1 mm. Shape: Elongated oblong. Apex: Mostly emarginate. Base: Attenuate and fused into a corolla tube. Margin: Entire. Orientation: Initially upright to eventually perpendicular. Texture, upper and lower surfaces: Smooth, glabrous; satiny. Number of ray florets per inflorescence: About 166 arranged in numerous whorls. Color: When opening and fully opened, upper surface: Close to 155D overlain with close to 77A; color is more faintly overlain with close to 77A with development. When opening and fully opened, lower surface: Close to 155D underlain with close to 77A to 79A; color is more faintly underlain with close to 77A to 79A with development.

*Disc florets.*—Arrangement: Massed at center of receptacle. Length: About 4 mm. Diameter, apex: About 1 mm. Diameter, base: About 1 mm. Shape: Tubular; elongated. Apex: Five-pointed. Number of disc florets per inflorescence: About twelve. Color: Immature: Close to 144A. Mature, apex: Close to 9A. Mature, mid-section: Close to 154D to 155D. Mature, base: Close to 155A.

*Phyllaries.*—Quantity per inflorescence: About 22 arranged in two to three whorls. Length: About 7 mm. Width: About 2.5 mm. Shape: Lanceolate. Apex: Acute. Base: Truncate. Margin: Entire. Texture, upper surface: Waxy, smooth. Texture, lower surface: Pubescent. Color, upper surface: Close to 146A. Color, lower surface: Close to 146A to more green than 147A.

*Peduncles.*—Length, terminal peduncle: About 3.9 cm. Length, fourth peduncle: About 5.8 cm. Diameter: About 2 mm. Angle: About 45° from vertical. Texture: Pubescent. Color: 146A.

*Reproductive organs.*—Androecium: Present on disc florets only. Anther length: About 1 mm. Anther color: Close to 9A. Pollen amount: None observed. Gynoecium: Present on both ray and disc florets. Style length: About 4 mm. Style color: Close to 154D. Stigma color: Close to 9A.

*Seed/fruit.*—Seed and fruit production has not been observed.

Disease/pest resistance: Plants of the new *Chrysanthemum* exhibited good resistance to *Fusarium oxysporum* and *Fusarium solani* in inoculated trials in 2005. Resistance to pests and other pathogens common to *Chrysanthemums* has not been observed on plants grown under commercial greenhouse conditions.

It is claimed:

1. A new and distinct cultivar of *Chrysanthemum* plant named 'Yochatham', as illustrated and described.

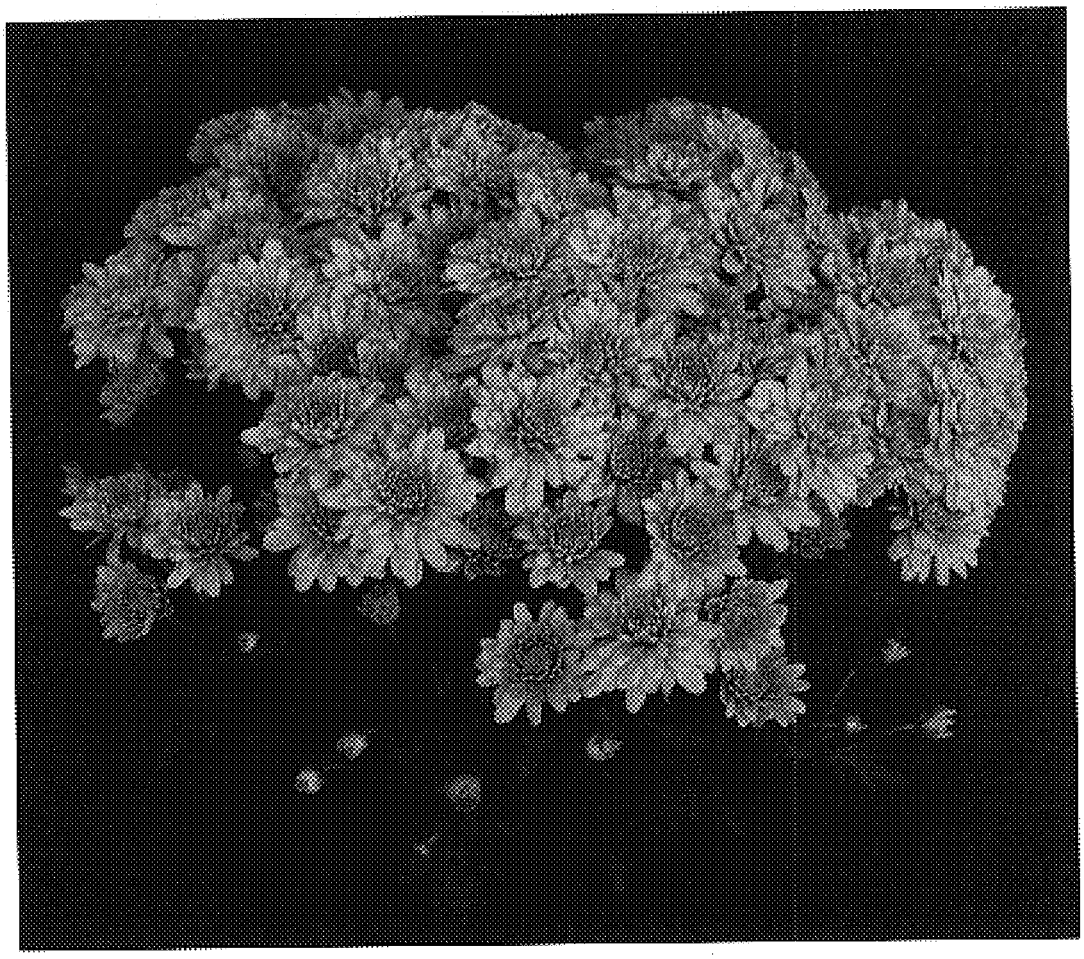

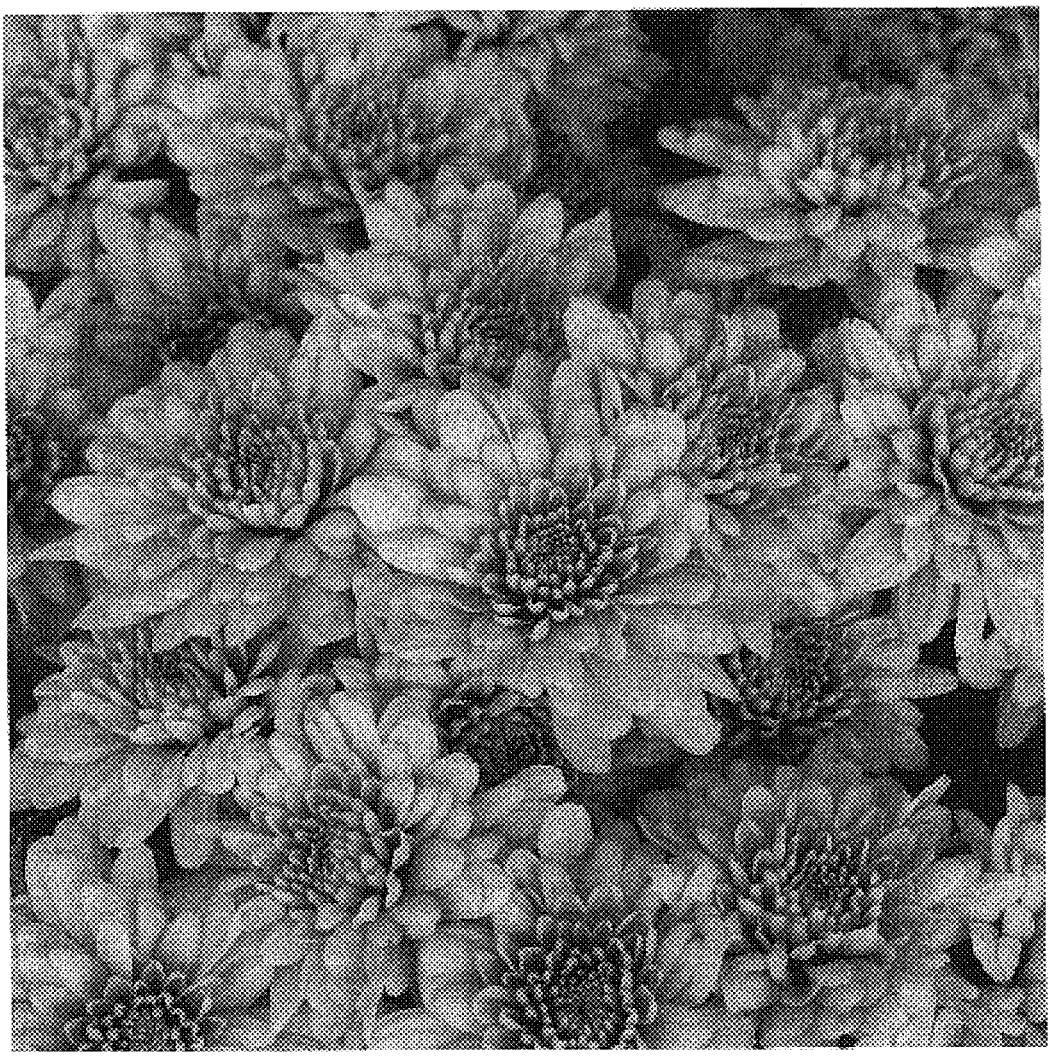

* * * * *